(12) United States Patent
Matsumura

(10) Patent No.: US 8,747,320 B2
(45) Date of Patent: Jun. 10, 2014

(54) ULTRASONIC DIAGNOSTIC APPARATUS

(75) Inventor: Takeshi Matsumura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 94 days.

(21) Appl. No.: 12/989,527

(22) PCT Filed: Apr. 14, 2009

(86) PCT No.: PCT/JP2009/057470
§ 371 (c)(1),
(2), (4) Date: Oct. 25, 2010

(87) PCT Pub. No.: WO2009/131028
PCT Pub. Date: Oct. 29, 2009

(65) Prior Publication Data
US 2011/0040186 A1 Feb. 17, 2011

(30) Foreign Application Priority Data

Apr. 25, 2008 (JP) ................................. 2008-116388

(51) Int. Cl.
A61B 8/00 (2006.01)

(52) U.S. Cl.
USPC ............................ 600/443; 600/447; 600/459

(58) Field of Classification Search
None
See application file for complete search history.

(56) References Cited

U.S. PATENT DOCUMENTS 6,003,378 A * 12/1999 Scherr et al. ..................... 73/703
6,500,126 B1 * 12/2002 Brock-Fisher ................ 600/459
7,242,793 B2 * 7/2007 Trobaugh et al. ............. 382/128
7,369,458 B2 * 5/2008 Sifferman et al. .............. 367/13

FOREIGN PATENT DOCUMENTS

| JP | 2005-66041 | | 3/2005 | |
| JP | 2006-247203 | | 9/2006 | |
| WO | WO 2005/120358 A1 | | 12/2005 | |
| WO | WO 2006/121031 A1 | | 11/2006 | |
| WO | WO 2008016022 | * | 2/2008 | ............... A61B 8/08 |

OTHER PUBLICATIONS

Talbi et al., Surface Acoustic Wave Pressure Sensor, Ferroelectrics, 2002, vol. 273, pp. 53-58.*
Lee et al., Surface Acoustic Wave Based Pressure Sensor with Ground Shielding over Cavity on 410 YX LiNbO3, Japanese Journal of Applied Physics, vol. 45, No. 7, 2006, pp. 5974-5980.*

* cited by examiner

Primary Examiner — Long V. Le
Assistant Examiner — Bo J Peng
(74) Attorney, Agent, or Firm — Antonelli, Terry, Stout & Kraus, LLP.

(57) ABSTRACT

The present invention is made to accurately detect an absolute pressure even when a contact property between an elastic coupler and a body surface of an object is poor. An elastic coupler 20 is formed by an elastic material with flexibility to have two layers at least with different ultrasonic wave reflectance properties and attached to an ultrasonic wave transmitter/receiver surface, and a pressure calculating unit 30 detects the position of a boundary surface 22 between those two layers based on RF signal frame data output from an RF signal frame data selection unit 10, obtains positional change of the boundary surface based on the detected position of the boundary surface and the initial position of the boundary surface, which was obtained in advance, and obtains the absolute pressure applied to the object based on the positional change and a pre-set elasticity property of the elastic coupler. At this time, for example, an ID code is given to the elastic coupler by making the initial position or the like of the boundary surface of the elastic coupler be different in accordance with the type of the elastic coupler, the pressure calculating unit 30 identifies the ID code, identifies the type of the elastic coupler with reference to a coupler database, and reads the elasticity property corresponding to the ID code.

15 Claims, 10 Drawing Sheets

FIG. 2
(A)
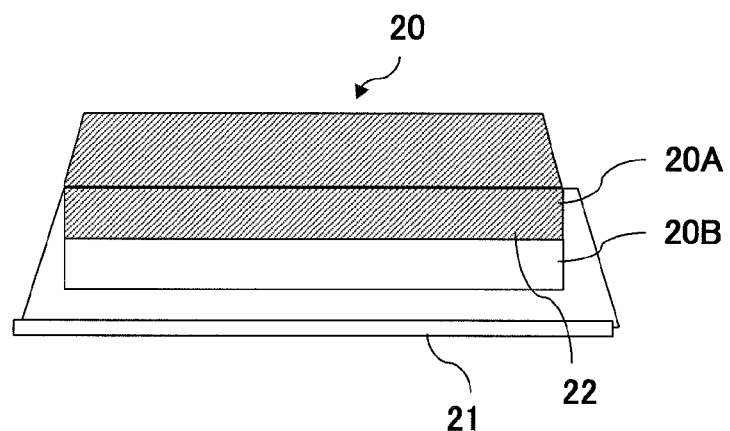
(B)
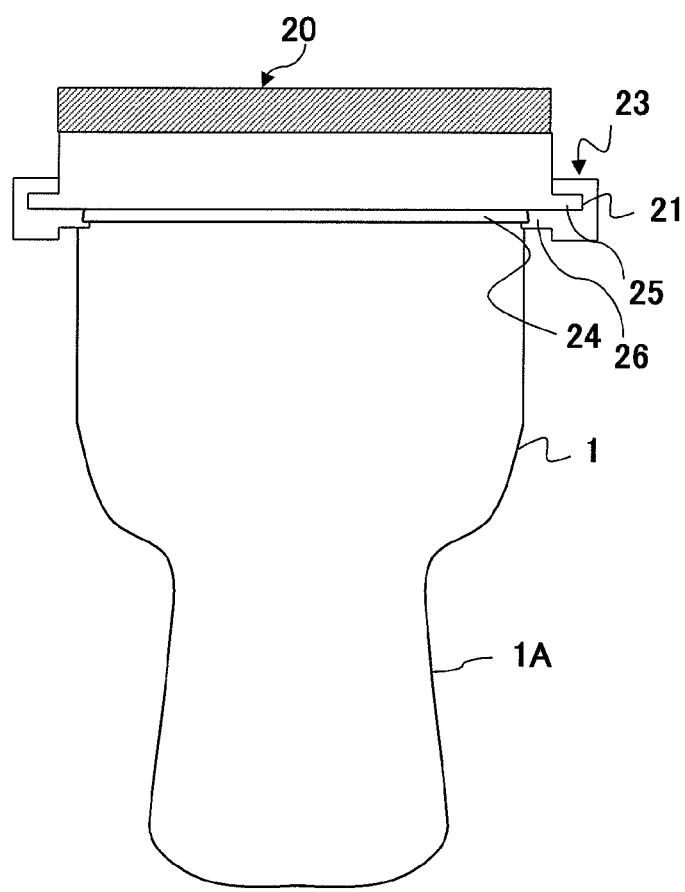

FIG. 3
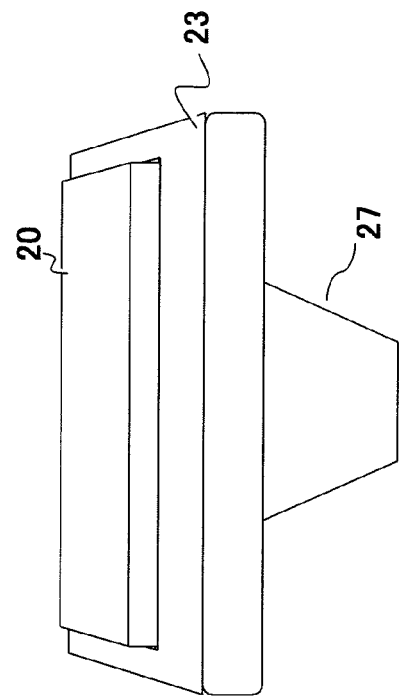
(B)
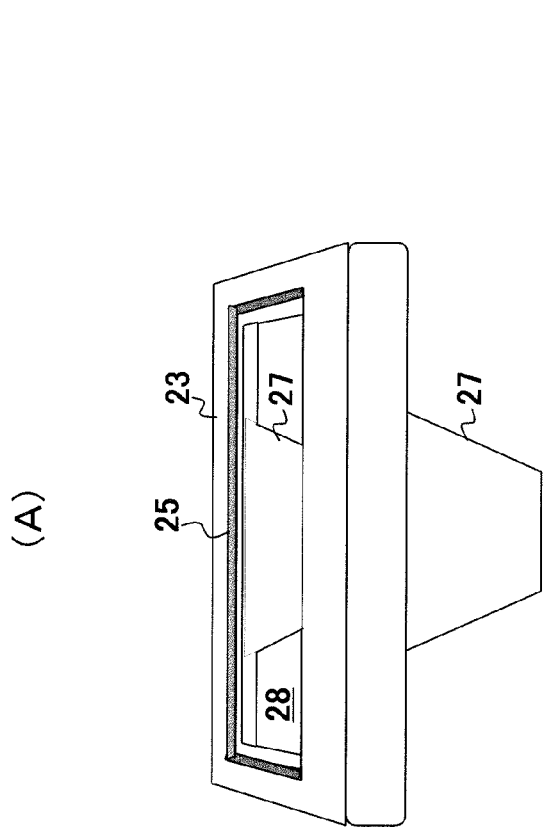
(A)

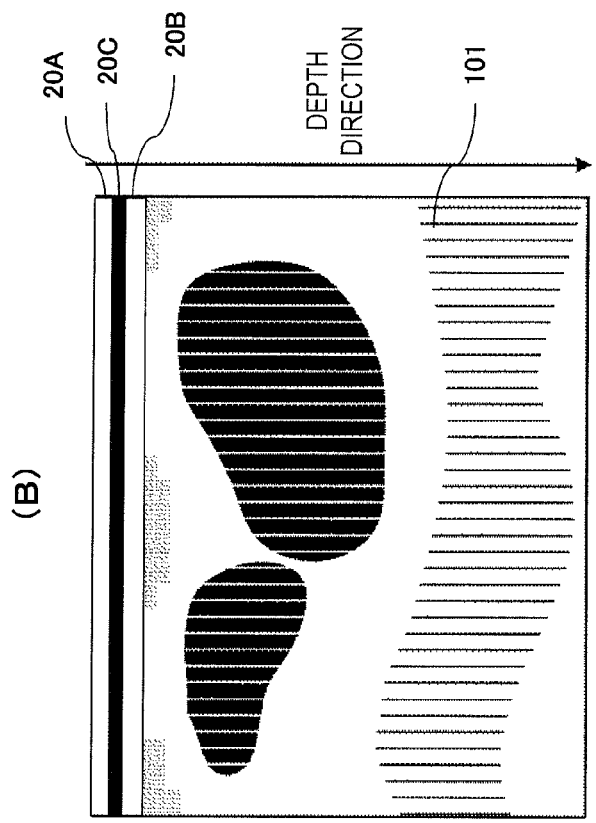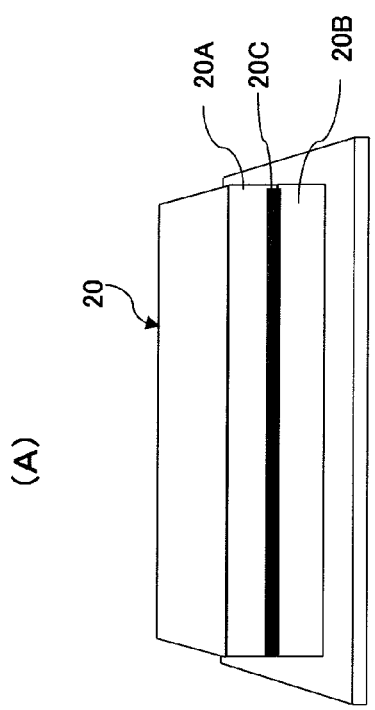
FIG. 9

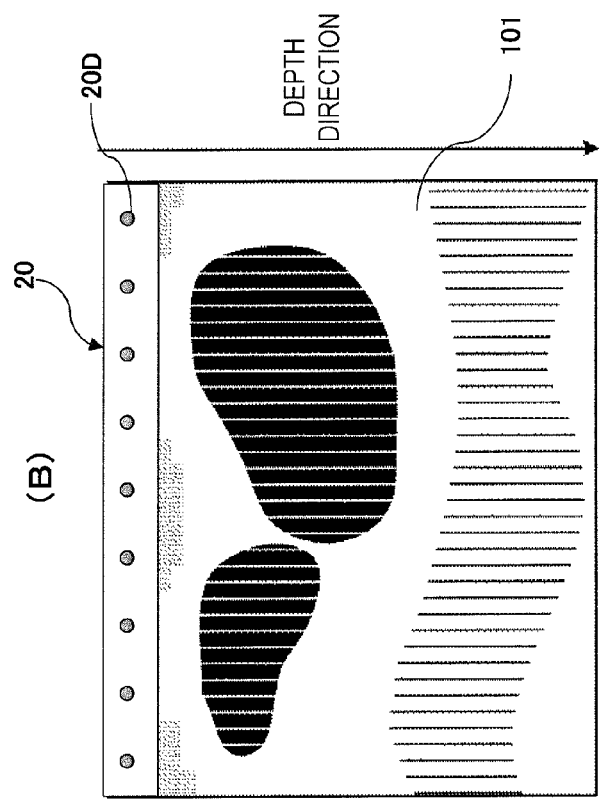
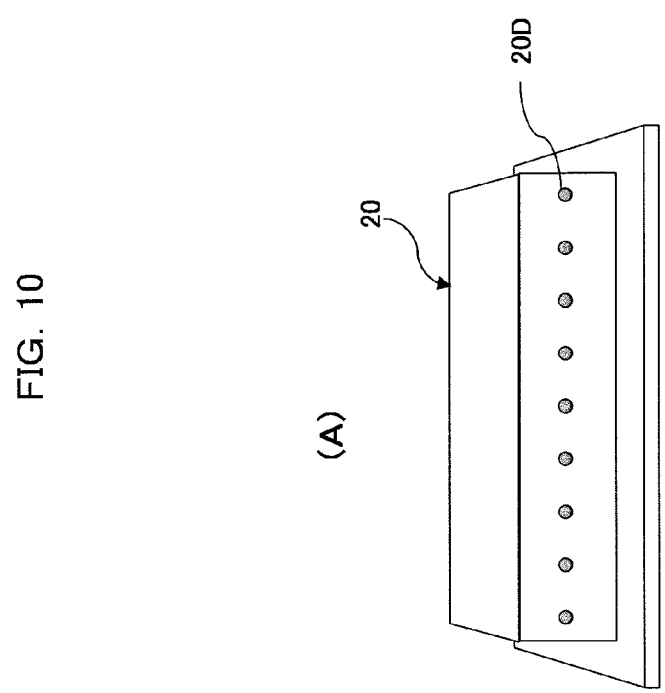
FIG. 10

ULTRASONIC DIAGNOSTIC APPARATUS

TECHNICAL FIELD

The present invention relates to an ultrasonic diagnostic apparatus, and particularly to a technique for making it possible to detect an absolute pressure to be applied to an object to be examined by an ultrasonic probe at the time of a test such as a diagnosis by a tomographic image (B mode image) or elastic information of a body tissue of an object, or a bloodstream diagnosis by Doppler measurement or a color flow mode (CFM).

BACKGROUND ART

Generally, an ultrasonic diagnostic apparatus is for performing a diagnosis such that ultrasonic waves are transmitted into a body of an object from an ultrasonic probe (hereinafter, simply referred to as a probe), a reflected echo signal of the ultrasonic waves which have been reflected from the inside of the body is received by the probe, and an image or the like which is suitable for the test of a tissue, a function, or the like inside the body is created based on the received reflected echo signal (RF signal).

In such an ultrasonic diagnostic apparatus, for the test by a B mode image, it is preferable to obtain an image with a high image quality by placing the probe on the object with a relatively strong force, pressing and deforming the body tissue so that the deep tissue can be closer to the probe, and imaging the tissue since the ultrasonic waves attenuate in the course of the propagation inside the body tissue. On the other hand, in the bloodstream test such as the Doppler measurement, the CFM, or the like, since it is not possible to obtain correct information on the bloodstream because the cross-section of the blood vessel is deformed when the probe is placed on and pressed against the body tissue with an excessively strong force, it is preferable to perform the test with the pressurizing state which is gentler than that at the time of the B mode diagnosis. In addition, since the body tissue has a nonlinearity in which the hardness of the tissue changes in accordance with the strength of the pressurizing even in the test by elastography for creating an image of elastic information regarding the hardness or the softness of the body tissue, it is important to perform a diagnosis based on an elasticity image obtained under a pressurizing state with a constant absolute pressure.

Accordingly, it is preferable to measure and display the absolute pressure applied to the body tissue in real time since there is a concern that an appropriate prompt diagnosis is hindered if the test proceeds in an inappropriate pressurizing state in various testing methods or when the testing method is changed, for example.

In order to measure an actual pressure to be applied to the body tissue of the object, that is, an absolute pressure to be applied to the body tissue (hereinafter, simply referred to as an absolute pressure), Patent Literature 1 discloses that the distortion of an elastic coupler is obtained with the use of a known displacement and distortion calculation based on a pair of RF signal frame data, which was obtained at different timings, and the obtained distortion is converted into the absolute pressure with the use of a pre-set elastic modulus of the elastic coupler.

Thus, according to the method of calculating the pressure disclosed in Patent Literature 1, it is possible to obtain the elastic information on the hardness or the softness of the body tissue by measuring the absolute pressure applied to the object, for example.

CITATION LIST

Patent Literature

PTL 1: JP-A-2005-66041

SUMMARY OF INVENTION

Problem to be Solved by the Invention

However, although it is basically possible to detect the absolute pressure with high sensitivity and high accuracy in the method of detecting the absolute pressure by the elastic coupler according to Patent Literature 1, there is still room for improvement as described below.

For example, when there is a part with irregular contact, in which fine unevenness, an air layer, or the like is interposed, due to a poor contact property between a contact surface of the elastic coupler on the side of the object and a body surface of the object, it is not possible to appropriately detect the boundary with the body surface of the object, and thereby it is not possible to appropriately detect the thickness of the elastic coupler in some cases. In addition, since the deformation in the contact part around the non-contact part becomes larger when there is a part with irregular contact, it is not possible to appropriately measure the distribution of the absolute value if the deformation and the distortion at the boundary part is measured and converted into the absolute pressure.

The object to be achieved by the present invention is to accurately perform the detection of the absolute pressure.

In addition to the above object, the object to be achieved by the present invention is to simplify the operation for detecting the absolute pressure with the use of an appropriate elastic coupler depending on the testing method or the like and thereby to enhance usability.

Means for Solving the Problem

As the first aspect of the present invention, in an ultrasonic diagnostic apparatus including an ultrasonic probe for transmitting and receiving ultrasonic waves while being in contact with an object, a transmitting unit for driving the ultrasonic probe, a receiving unit for receiving and processing an RF signal which is a reflected echo signal received by the ultrasonic probe, and an image creating unit for creating an ultrasonic image based on the RF signal output from the receiving unit, a pressure calculating unit for obtaining the pressure applied to the object based on the deformation of an elastic coupler which has been attached to an ultrasonic wave transmitter/receiver surface of the ultrasonic probe is provided, whereby the elastic coupler is formed to have at least two layers, and the pressure calculating unit detects the position of the boundary surface between the two layers, obtains the positional change of the boundary surface based on the detected position of the boundary surface and the initial position of the boundary surface which has been obtained in advance, and obtains absolute pressure based on the positional change and an elasticity property of the elastic coupler.

That is, the elastic coupler is formed to have at least two layers with different ultrasonic wave reflectance properties by an elastic material having flexibility, and the boundary surface between the layers with different ultrasonic wave reflectance properties is disposed between the attachment surface which is attached to the ultrasonic wave transmitter/receiver surface and the contact surface which is in contact with the body surface of the object. The pressure calculating unit is characterized by detecting the position of the boundary surface in the thickness direction of the elastic coupler based on the RE signal output from the receiving unit, obtaining the positional change of the boundary surface based on the detected position of the boundary surface and the initial position of the boundary surface, which was obtained in advance, and obtaining the absolute pressure applied to the object based on the positional change and the pre-set elasticity property of the elastic coupler.

Since the position of the boundary surface formed inside the elastic coupler is detected, and the absolute pressure is obtained based on the positional change, it is possible to stably detect the boundary surface inside the elastic coupler regardless of the contact property between the elastic coupler and the body surface of the object as compared with the case in which the boundary between the elastic coupler and the body surface of the object is detected. Accordingly, it is possible to accurately detect the absolute pressure. In addition, the initial position of the boundary surface in the initial state in which no pressurizing force is applied to the elastic coupler can be detected based on the RF signal output from a receiving unit in the same manner as in the positional detection of the boundary surface in the pressurized state in which the pressurizing force is applied.

In addition, in order to accurately perform the detection of the absolute pressure, in regard to the characteristic configuration of the second aspect of the present invention, although the elastic coupler is the same as that in the first aspect, the configuration of the pressure calculating unit is different from that in the first aspect. That is, the pressure calculating unit is characterized by detecting the displacement of the position of the boundary surface in the thickness direction of the elastic coupler based on the pair of RF signal frame data which was obtained at different timings and output from the receiving unit, obtaining the distortion of the boundary surface in the thickness direction based on the displacement, and obtaining the absolute pressure applied to the object based on the distortion in the thickness direction and the pre-set elasticity property of the elastic coupler.

With such a configuration, it is possible to stably detect the boundary surface inside the elastic coupler regardless of the contact property between the elastic coupler and the body surface of the object, and thereby to accurately detect the distortion of the boundary surface. Accordingly, it is possible to accurately detect the absolute pressure based on the relation between the distortion and the elasticity property.

Furthermore, in the second aspect, the pressure calculating unit can sum up the distortions of the boundary surface in the thickness direction from the initial state, in which no pressure is applied to the elastic coupler, over the passage of time and obtain the absolute pressure applied to the object based on the summed-up value of the distortion and the pre-set elasticity property of the elastic coupler. With such a configuration, since the distortions of the boundary surface in the thickness direction are summed up, it is possible to further precisely detect the distortions of the boundary surface, and thereby to further accurately detect the absolute pressure based on the relation between the distortion summed-up value and the elasticity property.

In the first or second aspect, a configuration can be made such that the elastic coupler is formed to have a thin intermediate layer interposed between the boundary surfaces of the two layers, and the ultrasonic wave reflectance property of the intermediate layer is formed to be different from those of the other two layers. In this case, the intermediate layer can be extended in a direction perpendicular to the scanning direction of the ultrasonic beam of the ultrasonic probe and be configured by a plurality of linear ultrasonic wave reflection bodies which are spaced from each other.

If the intermediate layer is provided in the elastic coupler, the pressure calculating unit of the first aspect can be configured so as to detect the position of the intermediate layer in the thickness direction, obtain the positional change of the intermediate layer based on the detected position of the intermediate layer and the pre-set initial position of the intermediate layer, and obtain the absolute pressure applied to the object based on the positional change and the pre-set elasticity property of the elastic coupler.

In addition, if the intermediate layer is provided in the elastic coupler, the pressure calculating unit of the second aspect can be configured so as to detect the displacement of the position of the intermediate layer of the elastic coupler in the thickness direction based on the pair of RF signal frame data which was obtained at different timings and output from the receiving unit, obtain the distortion of the intermediate layer in the thickness direction based on the displacement, and obtain the absolute pressure applied to the object based on the distortion in the thickness direction and the pre-set elasticity property of the elastic coupler. Moreover, the pressure calculating unit of the second aspect can be configured so as to sum up the distortions of the intermediate layer in the thickness direction from the initial state in which no pressure is applied to the elastic coupler over the passage of time and obtain the absolute pressure applied to the object based on the distortion summed-up value and the pre-set elasticity property of the elastic coupler.

Furthermore, a configuration is possible in which the elastic coupler is formed to have a two-layer structure, in which the layer on the side of the contact surface which is in contact with the body surface of the object is thinner and has a stronger ultrasonic wave reflectance property. In addition, the elastic coupler can be configured such that the ultrasonic wave attenuation property is greater by mixing ultrasonic scattering bodies into the elastic material.

On the other hand, in order to achieve the object of simplifying the operation for detecting the absolute value with the use of an appropriate elastic coupler depending on the testing method or the like and enhancing usability, the elastic coupler of the first or second aspect is configured such that the position of the boundary surface between the two layers in the thickness direction is made to be different depending on the type of the elastic coupler and an identification code is formed with which the type of the elastic coupler can be identified with the RF signal. The pressure calculating unit in this case can be configured so as to identify the type of the elastic coupler by detecting the identification code based on the RF signal or the RF signal frame data and obtain the absolute pressure based on the elasticity property which was set to correspond to the type of the elastic coupler.

With this configuration, it is possible to automatically identify the type of the elastic coupler in the state, in which the elastic coupler is attached to the ultrasonic probe, by the pressure calculating unit when a plurality of elastic couplers with different elasticity properties are prepared, and the elastic coupler is replaced with the one which is suitable for the appropriate measurement of the absolute pressure in accordance with the testing method, the depth of the site of interest, or the like. Accordingly, it is possible to calculate the absolute pressure in a manner matching with the elasticity property of the type of the elastic coupler if the elasticity property in accordance with the type of the elastic coupler is stored in advance in the pressure calculating unit.

In addition, in regard to the identification code, the position of the boundary surface between the two layers in the thickness direction can be configured to differ. In such a case, the pressure calculating unit can be configured to identify the type of the elastic coupler based on the depth distribution pattern of the RF signal in a coupler echo region based on the RF signal or the RF signal frame data.

In addition, in regard to the identification code, a configuration can be made such that the ultrasonic scattering bodies are formed while being encoded and dispersed in at least one of the scanning direction and the thickness direction in the regions on the both sides of the elastic coupler in the scanning direction. In such a case, the pressure calculating unit can be configured to identify the type of the elastic coupler from the pattern of the RF signal in the region on the both sides of the elastic coupler based on the RF signal or the RF signal frame data.

Here, the elasticity property set in the coupler database can be at least one of an elastic modulus, a relation curve between the deformation in the thickness direction and the elastic modulus, a relation curve between the distortion in the thickness direction and the elastic modulus, a relation curve between the summed-up value of the deformation or the distortion in the thickness direction and the elastic modulus, and an elastic modulus correction coefficient with respect to the deformation or the distortion in the thickness direction.

Advantageous Effects of Invention

According to the present invention, it is possible to accurately detect the absolute pressure. In addition, the operation is simplified, and usability is enhanced.

BRIEF DESCRIPTION OF DRAWINGS

FIG. 2 is a configuration diagram of an example of an elastic coupler.
FIG. 3 is a configuration diagram of an example of an attachment tool of the elastic coupler.
FIG. 9 is a configuration diagram of another example of the elastic coupler and a diagram illustrating the ultrasonic image of the elastic coupler.
FIG. 10 is a configuration diagram of still another example of the elastic coupler and a diagram illustrating the ultrasonic image of the elastic coupler.

REFERENCE SIGNS LIST

Figure 1:
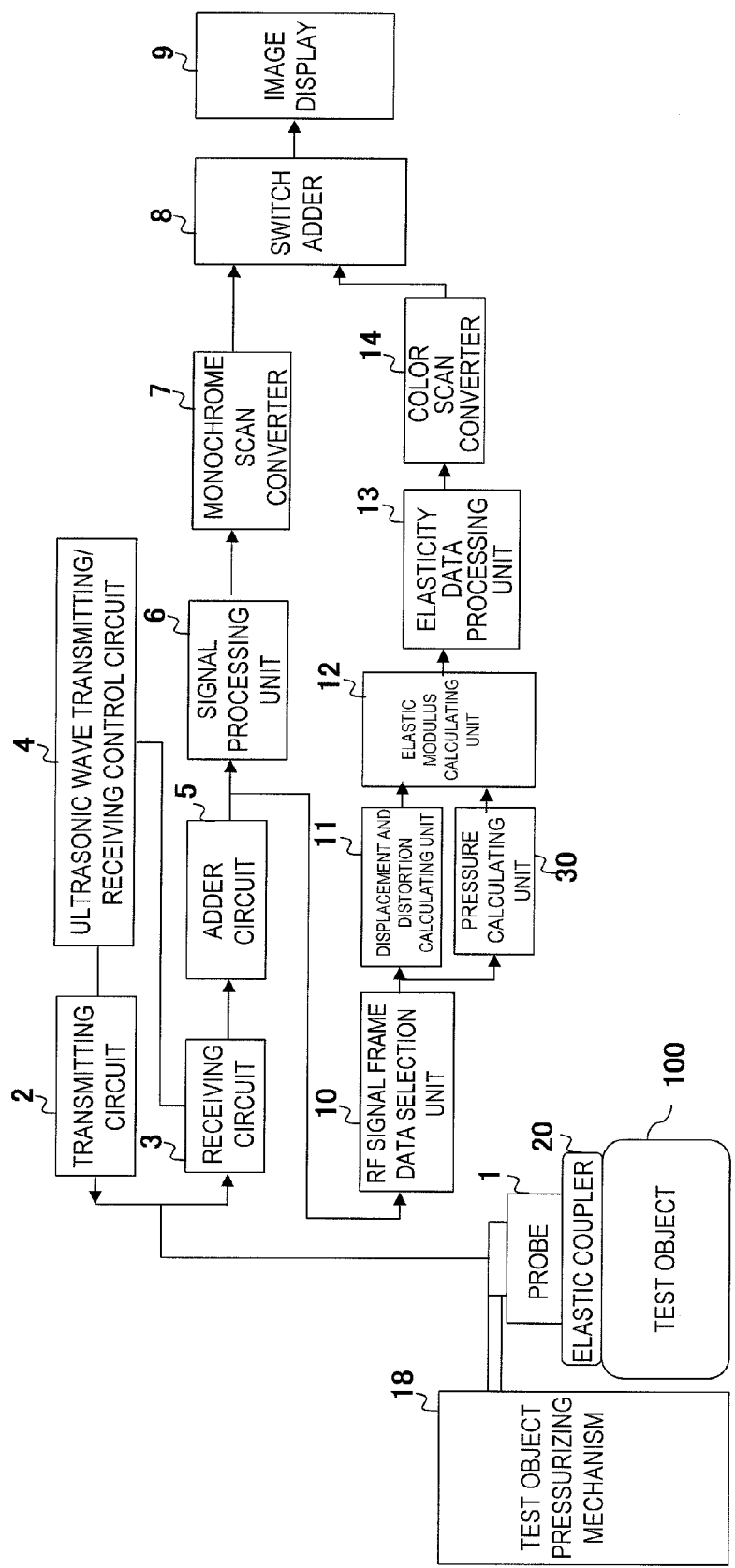
FIG. 1 is a block configuration diagram of an ultrasonic diagnostic apparatus of embodiment of the present invention.

1: Probe
2: Transmitting Circuit
3: Receiving Circuit
8: Switch Adder
9: Image Display
10: RF Signal Frame Data Selection Unit
11: Displacement and Distortion Calculating unit
12: Elasticity Modulus Calculating unit
13: Elasticity Data Processing Unit
20: Elastic Coupler
30: Pressure Calculating unit
31: Coupler ID Identification Unit
32: Initialization Processing Unit
33: Coupler Distortion Calculating unit
34: Pressure converter
35: Pressurizing-State Image Constructing Unit
36: Coupler Database

MODES FOR CARRYING OUT THE INVENTION

Hereinafter, a description will be made of the embodiments of the ultrasonic diagnostic apparatus according to the present invention with reference to the drawings.

FIG. 1 shows a functional block configuration diagram of an embodiment in which the present invention is applied to an ultrasonic diagnostic apparatus for performing the test based on elastic information.

As shown in FIG. 1, the ultrasonic diagnostic apparatus of this embodiment is for obtaining a tomographic image of a site as a diagnostic target of the object with the use of ultrasonic waves and obtaining an elasticity image representing the hardness or the softness of the body tissue. As shown in the same drawing, an ultrasonic probe (hereinafter, simply referred to as a probe) 1 is electrically connected to a transmitting circuit 2 and a receiving circuit 3. As is well known, the probe 1 is a generation source of the ultrasonic waves and is formed such that a plurality of oscillators for receiving the waves of reflected echo are arranged in a strip shape. Each oscillator generally has a function of converting an ultrasonic signal of input pulse waves or continuous waves into ultrasonic waves and emitting the ultrasonic waves and a function of converting reflected echo emitted from the inside of an object 100 into a reflected echo signal which is an electric signal and outputting the reflected echo signal.

The transmitting circuit 2 is configured such that the transmitting circuit 2 and the receiving circuit 3 are cooperatively controlled by an ultrasonic wave transmitting/receiving control circuit 4. The ultrasonic wave transmitting/receiving control circuit 4 is for controlling the timing at which the ultrasonic waves are transmitted and received, controls the transmitting circuit 2 to radiate an ultrasonic wave transmitting beam suitable for the targeted ultrasound test from the probe 1 into the object 100, and controls the receiving circuit 3 to receive a desired ultrasonic wave receiving beam from the probe 1. The ultrasonic wave transmitting/receiving control circuit 4 of this embodiment controls the transmitting circuit 2 and the receiving circuit 3 to scan the ultrasonic wave transmitting beam along a cross-sectional plane so as to form the ultrasonic wave transmitting beam and the ultrasonic wave receiving beam suitable for the measurement of a B mode tomographic image.

The receiving circuit 3 amplifies the reflected echo signal, which has been received by the probe 1, at a predetermined gain. The reflected echo signals, the number of which corresponds to the number of the amplified oscillators, are input to an adder circuit 5. The adder circuit 5 adds the total of the phases of the plurality of reflected echo signals which have been amplified by the receiving circuit 3 and creates RF signal frame data corresponding to the cross-sectional plane.

A signal processing unit 6 inputs the RF signal frame data output from the adder circuit 5 and performs various kinds of signal processing such as gain correction, log correction, wave detection, contour enhancement, and filter processing to create image data. A monochrome scan converter 7 is configured to include cross-section scanning means for obtaining the image data, which has been output from the signal processing unit 6, in a sonic period and reads the image data in a frequency based on the television scheme for displaying this ultrasonic image and means for controlling the system including, for example, an A/D converter for converting the image data from the signal processing unit 6 into a digital signal, a plurality of frame memories for storing the image data which has been converted into a digital signal by this A/D converter in a time series manner, a controller for controlling these operations, and the like. The image data for a B mode image, for example, in a time series manner, which has been created by the monochrome scan converter 7 is output to an image display 9 via a switch adder 8. The image display 9 includes a D/A converter for converting the image data output from the monochrome scan converter 7 into an analog signal and a color television monitor for displaying the analog video signal output from this D/A converter as an image.

Next, a description will be made of the process for creating an elasticity image and causing the image display 9 to display the elasticity image according to this embodiment. Generally, the deformation of a body tissue due to a pressure (stress) applied to the body tissue of the site as a diagnostic target by pressurizing the object 100 with the probe 1 is used in order to create the elasticity image. That is, a degree of the deformation differs depending on the elasticity, which is the hardness or the softness of the body tissue, even when the same stress acts on the body tissue. Thus, the elasticity image, with which a normal site and a site of disease can be identified, is created by performing the ultrasonic wave transmitting/receiving with the probe 1 and obtaining the degree of the deformation of the tissue with the use of the RF frame data corresponding to a pair of B mode images at the time of pressurizing the object 100 by the probe 1 with different pressures.

In this embodiment, the RF signal frame data created by the adder circuit 5 is input to an RF signal frame data selection unit 10. The RF signal frame data selection unit 10 sequentially accumulates the RF signal frame data, which is sequentially output from the adder circuit 5, in a frame memory. Then, in response to a command from a control unit which is not illustrated, the RF signal frame data selection unit 10 selects, for example, the latest RF signal frame data and one piece of RF signal frame data from among the plural pieces of RF signal frame data in the past and outputs a pair of RF signal frame data obtained at different timings to a displacement and distortion calculating unit 11. In addition, the RF signals may be signals with forms of I and Q signals which have been subjected to code demodulation.

The displacement and distortion calculating unit 11 executes a one-dimensional or two-dimensional correlation processing with respect to the pair of RF signal frame data output from the RF signal frame data selection unit 10 and calculates the displacement (or the displacement vector) of a plurality of measurement points i and j which have been set respectively in the scanning direction and in the depth direction of the ultrasonic beam of the RF signal frame data. The calculated displacement data at the plurality of measurement points is created as displacement frame data. In addition, as a method of the displacement calculation, known methods including a block matching method and a gradient method can be used as disclosed in Patent Literature 1, for example, in addition to the correlation processing. The block matching method is a method in which a marked block including a plurality of pixels around a pixel at the marked measurement point is set, the block with the image information closely resembles that of the marked block is searched while moving with respect to the frame before the displacement, and the displacement is regarded as from the position of the block which most closely resembles to the current position.

The displacement and distortion calculating unit 11 calculates the distortion of the respective measurement points by spatially differentiating the displacement of the respective measurement points with the use of the displacement frame data as is already known. The distortion frame data is created based on the distortion at the respective measurement points which have been obtained by the calculation and output to an elastic modulus calculating unit 12.

Furthermore, the elastic modulus calculating unit 12 calculates elastic modulus (for example, Young's modulus) at the respective measurement points by a known method based on the distortion at the respective measurement points of the input distortion frame data and based on the absolute pressure (stress), which is given from a pressure calculating unit 30, which will be described later, and which is acting on the respective measurement points i and j. Elastic modulus frame data is created based on the elastic modulus at the respective measurement points obtained by the calculation and is output to an elasticity data processing unit 13. The elasticity data processing unit performs various kinds of image processing such as smoothing processing in a frame, contrast optimization processing, and smoothing processing in a time axis direction between frames with respect to the elasticity frame data of the elastic modulus or the distortion created by the elastic modulus calculating unit 12 and outputs the processed data to a color scan converter 14.

The color scan converter 14 creates elasticity image data by adding color phase information of red, green, blue, or the like to the pixel corresponding to the respective measurement points based on the elasticity frame data output from the elasticity data processing unit 13. For example, in the distortion frame data output from the elasticity data processing unit 13, the pixel for which large distortion has been measured is converted into a red code within the elasticity image data, and on the other hand, the pixel for which small distortion has been measured is converted into a blue code within the elasticity image data. The elasticity image data is created by adding color phase information to the respective pixels in the case of the elastic modulus frame data as well. In addition, it is also possible to add an illuminance level corresponding to the size of the distortion or the like with the use of the monochrome scan converter instead of the color scan converter 14.

The elasticity image data created by the color scan converter 14 is output to the switch adder 8. The switch adder 8 receives the monochrome tomographic image data output from the monochrome scan converter 7 and the color elasticity image data output from the color scan converter 14, adds or shifts both the images in response to the input command, and outputs the added or shifted images to the image display 9. Specifically, it is possible to cause the image display 9 to switch and display only the monochrome tomographic image data, only the color elasticity image data, or both the images in an aligned manner. In addition, it is possible to switch the output image in response to the input command, for example, by allowing the image display 9 to perform the additive synthesis on both pieces of image data, that is, to create half-transparent overlapping images and to output and display the obtained image.

Next, a description will be made of the detailed configurations of an elastic coupler 20 and a pressure calculating unit 30, which are the characteristic units of this embodiment.

FIG. 2 shows an example of the elastic coupler 20. The elastic coupler 20 is formed in a plate shape from a gel-like material which is an elastic material with flexibility and is formed to have a brim portion 21 around one surface as shown in the perspective view of FIG. 2(A). The gel-like material forming the elastic coupler 20, in which an ultrasonic attenuation is small similar to an acoustic combining material, an acoustic lens material, and the like, and the sonic speed and the acoustic impedance are close to those in the body, and which has an excellent acoustic combining property with the body, is preferable as described in Patent Literature 1. In addition, it is preferable to use a material which is excellent in a shape retention property, flexibility, appropriate elasticity, and a shape restoration property. Particularly, the elastic coupler 20 of this example is formed to have two layers 20A and 20B with different ultrasonic wave reflectance properties as shown in the drawing, and a boundary surface 22 between those layers 20A and 20B is disposed between an attachment surface which is attached to the ultrasonic wave transmitter/receiver surface of the probe 1 and a contact surface which is in contact with the body surface of the object 100.

In addition, it is preferable to use a material for the elastic coupler 20 which does not generate a gap even when the elastic coupler 20 comes in contact with a part with unevenness such as a contact surface with the ultrasonic wave transmitter/receiver surface and the body surface of the object 100 even in the case where the elastic coupler 20 is attached to the ultrasonic wave transmitter/receiver surface of the probe 1. That is, if a gap is generated between the ultrasonic wave transmitter/receiver surface and the body surface, the ultrasonic waves irradiated from the probe 1 are reflected at the boundary of the air at the gap and becomes noise in the ultrasonic image. For example, it is possible to use aqueous gel (hydrogel) constituted by water and aqueous polymers such as gelatin, agar, oil gel, acrylamide, or polyvinyl alcohol, polyurethane, oil gel obtained by cross-linking and molding a composition containing rubber and oily component, and rubber obtained by molding and cross-linking a composition containing rubber with a low molecular weight blended as plasticizer into crude rubber.

The elastic coupler 20 formed in this manner is used while being attached to an ultrasonic wave transmitter/receiver surface 24 of the probe 1 with an attachment tool 23. That is, the attachment tool 23 is formed from resin or the like to have a frame shape with a groove 25 formed so as to match the brim portion 21 of the elastic coupler 20 as shown in FIG. 3(A). In addition, locking claws 26 for locking in the outer peripheral portion of the ultrasonic wave transmitter/receiver surface 24 are formed inside the frame body of the attachment tool 23. Moreover, a pair of gripped pieces 27 is formed on the opposing long sides of the frame body, and the top surface is formed with an opening 28 into which the elastic coupler 20 is inserted. In the thus formed attachment tool 23, the elastic coupler 20 is inserted into the opening 28 from the bottom as shown in FIG. 3(B), the brim portion 21 of the elastic coupler 20 is pushed into the groove 25 of the frame body, assembled therein, and used while being attached to the ultrasonic wave transmitter/receiver surface 24 of the probe 1. At this time, jelly or the like is interposed between the contact surfaces of the bottom surface of the elastic coupler 20 and the ultrasonic wave transmitter/receiver surface 24 and attached to the ultrasonic wave transmitter/receiver surface 24 of the probe 1 so as not to generate a gap therebetween, and the locking claws 26 are hooked to the outer periphery portion of the ultrasonic wave transmitter/receiver surface 24 and firmly fixed.

The ultrasound test is performed while gripping a gripped portions 1A of the probe 1 to which the elastic coupler 20 has been attached in the above manner and placing the exposure surface of the elastic coupler 20 on the body surface of the object 100. In addition, as shown in FIG. 1, it is also possible to cause an object pressurizing mechanism 18 to grip the gripped portion 1A of the probe 1 and to apply the pressurizing force to the body surface of the object 100.

Figure 4:
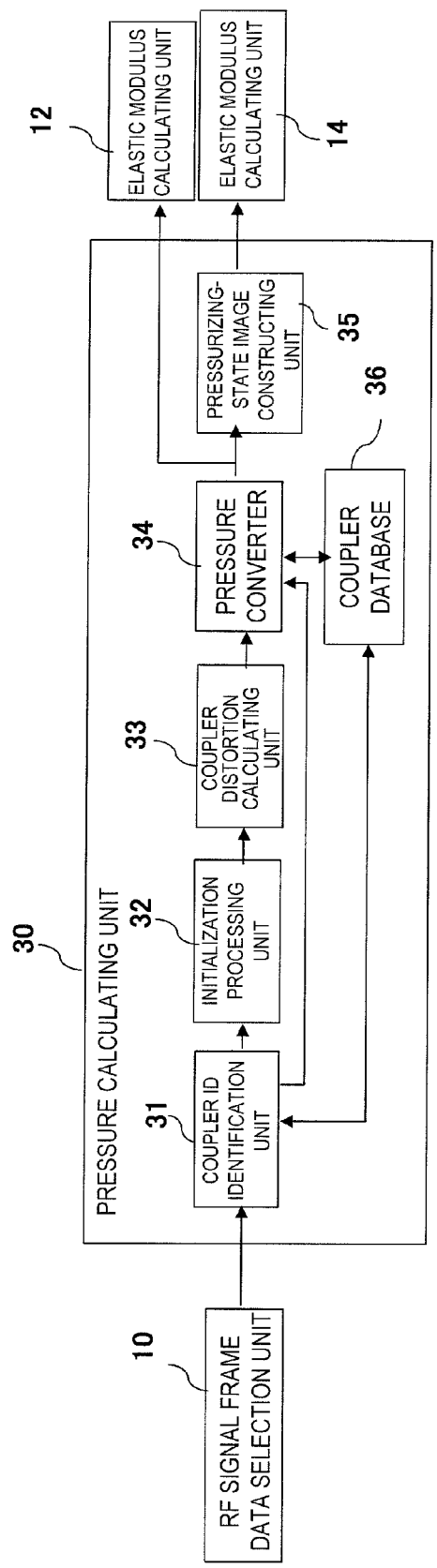
FIG. 4 is a block configuration diagram illustrating a detailed configuration of a pressure calculating unit of the embodiment.

The pressure calculating unit 30 is configured to have blocks shown in FIG. 4. That is, the pressure calculating unit 30 is configured to have a coupler ID identification unit 31, an initialization processing unit 32, a coupler distortion calculating unit 33, a pressure converter 34, a pressurizing-state image constructing unit 35, and a coupler database 36.

Although the elastic coupler 20 which is applied to this embodiment has the same shape as that shown in FIG. 2(A), the elastic coupler 20 is used while an identification code (ID) is given to the same type of the elastic coupler 20 by causing the depth of the boundary surface 22 or the reflectance properties of the layer 20A and 20B to be different for each type of the elastic coupler 20 depending on the purpose of use, in order to make it possible to automatically identify the type of the elastic coupler 20.

The coupler ID identification unit 31 receives the RF signal frame data from the RF signal frame data selection unit 10, detects the existence of the boundary surface 22, and detects that the elastic coupler 20 has been attached to the probe. Moreover, the coupler ID identification unit 31 determines the depth distribution of the RF signal or the like within the coupler echo region to detect the depth of the boundary surface 22 and automatically identify the ID code of the elastic coupler 20 with reference to the coupler database 36. The identified ID code is output to the pressure converter 34. In addition, the ID code is set to correspond to the depth of the boundary surface 22 and the positional pattern in the depth direction by input means, which is not illustrated, and the elasticity property is further set to correspond to the ID code in the coupler database 36.

The initialization processing unit 32 detects that the elastic coupler 20 is in the initial state with no pressure being applied based on the intensity change in the RF signal of the RF signal frame data and obtains an initial thickness of the elastic coupler 20 based on the RF signal when the elastic coupler 20 is in the initial state.

The coupler distortion calculating unit 33 detects the position of the boundary surface 22 of the elastic coupler 20 in the thickness direction based on the RF signal frame data, and detects the positional change of the boundary surface 22 in the thickness direction, and obtains the displacement and distortion of the boundary surface 22. The obtained displacement or distortion is output to the pressure converter 34 along with the ID code.

The pressure converter 34 reads the elasticity property corresponding to the input ID code from the coupler database 36 and converts the displacement or the distortion input from the coupler distortion calculating unit 33 into the absolute pressure based on the read elasticity property.

The pressurizing-state image construction unit 35 constructs the pressurizing-state image in order that the absolute pressure output from the pressure converter 34 is displayed on the image display 9.

Figure 5:
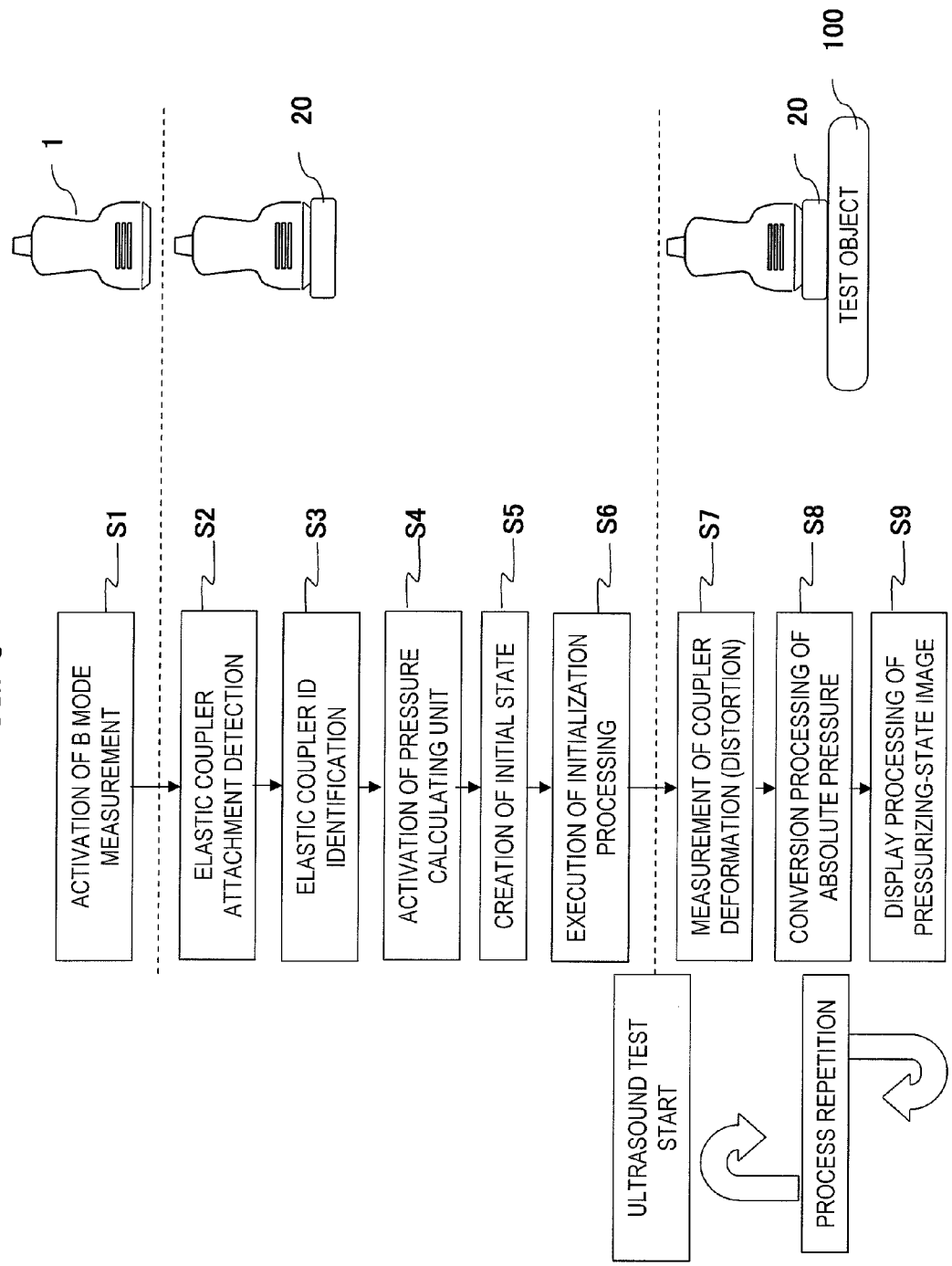
FIG. 5 is a flow chart illustrating process steps of a characteristic unit of the embodiment.

Hereinafter, a detailed description will be made of the pressure calculation processing by a pressure calculating unit 50 according to the embodiment with reference to the flow chart shown in FIG. 5.

[S1: Activation of Ultrasonic Diagnostic Apparatus]

The ultrasonic diagnostic apparatus is manually activated. The test mode is for a test by a B mode tomographic image, for example.

[S2: Coupler Attachment and Detection]

The elastic coupler 20 is attached manually to the ultrasonic wave transmitter/receiver surface 24 of the probe 1 as shown in FIG. 2(B). It is possible to automatically recognize the detection of whether or not the elastic coupler 20 has been attached by receiving the RF signal frame data by the coupler ID identification unit 31 based on whether or not the existence of the boundary surface 22 could be detected from the intensity distribution or the like of the RF signal. In addition, it is also applicable that the operator inputs to the coupler ID identification unit 31 via input means, which is not illustrated, the fact that the elastic coupler 20 has been attached.

[S3: Identification of Coupler ID]

Figure 6:
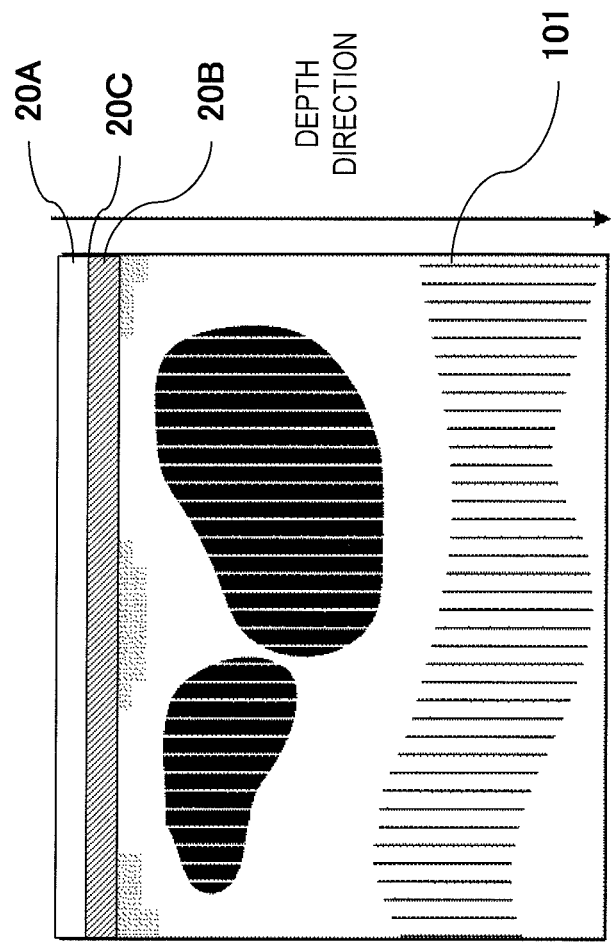
FIG. 6 is a diagram illustrating an ultrasonic image of the elastic coupler shown in FIG. 2.

The coupler ID identification unit 31 receives RF signal frame data from the RF signal frame data selection unit 10, detects the existence of the boundary surface 22, then detects the depth position of the boundary surface 22 by determining the depth distribution of the RF signal or the like within the coupler echo region, and automatically identifies the ID code of the elastic coupler 20 with reference to the coupler database 36. The identified ID code is output to the pressure converter 34. FIG. 6 shows an example of a B mode image 101 obtained by attaching the elastic coupler 20. As shown in the drawing, echo image of the two layers 20A and 20B and the boundary surface 22 of the elastic coupler 20 appears in the upper part of the image. Accordingly, it is possible to detect the position of the boundary surface 22 and automatically identify the ID code by detecting the position in the coupler echo region, at which the RF signal suddenly changes.

[S4: Activation of Pressure Calculating Unit]

The pressure calculating unit 30 is activated after the coupler ID identification unit 31 detects the ID code of the elastic coupler 20.

[S5: Creation of Initial State]

Although an initial position $D(0)$ of the boundary surface 22 of the elastic coupler 20 in the depth direction can be measured in advance, it is considered that the initial position $D(0)$ of the boundary surface 22 is reduced due to the temporal change such as evaporation or the like of the liquid component in the gel-like material which is a material of the elastic coupler 20. For this reason, it is preferable to automatically measure the initial position $D(0)$ of the boundary surface in the initial state every time the ultrasound test is performed in order to accurately detect the absolute pressure.

In this embodiment, the initial state in which the operator grips the probe 1 and holds it in the air can be automatically recognized by the initialization processing unit 32 in order to automatically measure the initial position $D(0)$ of the boundary surface in the initial state with no pressure being applied, in which the exposure surface of the elastic coupler 20 is held in the air. This initial state with no pressure being applied can be detected by the multiple echo signal included in the RF signal. That is, the multiple echo is generated due to a sudden change of the acoustic impedance at the boundary between the exposure surface of the acoustic lens and the air or the boundary between the exposure surface of the elastic coupler 20 and the air. For example, if the ultrasonic beam for the B mode test is transmitted while the probe 1 is held in the air in the state in which the elastic coupler 20 is not attached to the probe 1, the RF signal including the periodical multiple echo originated from the acoustic lens (with the thickness of about 1 mm) is received in the depth region which is close to the ultrasonic wave transmitter/receiver surface. On the other hand, if the elastic coupler 20 (with the thickness of about 5 to 10 mm, for example) is attached, the multiple echo originated from the acoustic lens disappears, and the multiple echo with a relatively long frequency, which is originated from the elastic coupler 20, is received. Thus, it is possible to automatically recognize that the elastic coupler 20 is held in the initial state with no pressure being applied by detecting the existence and the frequency of the multiple echo.

In addition, it is possible to manually order the coupler thickness calculating unit from the input means, which is not illustrated, to perform the automatic measurement of the initial position $D(0)$ of the boundary surface 22 in the state where the operator grips the probe 1 and holds it in the air instead of the automatic recognition of the initial state.

[S6: Execution of Initialization Processing]

The initialization processing unit 32 performs the automatic measurement of the initial position $D(0)$ of the boundary surface when the initial state of the elastic coupler 20 is recognized or when the command is input.

The initialization processing unit 32 obtains an average value J of a coordinate j at which an intensity $Q_{ij}$ of the RF signal (or the illuminance) becomes greater or smaller than a pre-set threshold value $Q_{thres}$ for measurement points ij at a coordinate i (i=0 to n) in the scanning direction of the ultrasonic beam, which is the alignment direction (long axis direction) of the oscillators of the probe 1 of the elastic coupler 20, and at the coordinate j (j=0 to m) in the depth direction, and sets the average value J as the initial position $D(0)$ of the boundary surface 22. In addition, since the coordinate J is a concept of time from the point in time when the ultrasonic waves are transmitted from the ultrasonic wave transmitter/receiver surface to the point in time when the ultrasonic waves reach the coordinate J and then returns to the ultrasonic wave transmitter/receiver surface, the initial position $D(0)$ of the boundary surface of the elastic coupler 20 can be calculated by $D(0)=J\times C/2$ when the speed of sound within the elastic coupler 20 is represented by C.

In addition, the initialization processing unit 32 can receive the illuminance data or the signal intensity of the B mode image output from the signal processing unit 6 instead of the RF frame signal output from the RF signal selection unit 10 and detect the initial position $D(0)$ of the boundary surface of the elastic coupler 20 by the same processing.

In other words, it is possible to detect the initial position $D(0)$ of the boundary surface by obtaining a time $t_i(0)$ for which the intensity of the RF signal changes significantly after the ultrasonic waves are transmitted from the transmitting circuit 2 to the probe 1. Since $t_i(0)$ is the time for the round trip of the ultrasonic waves which are reflected from the boundary surface of the elastic coupler 20, it is possible to obtain an initial position $D_i(0)$ of the boundary surface, which is a one-dimensional distribution in the scanning direction, by multiplying $t_i(0)$ by the speed of sound C and dividing the obtained value by 2. In addition, it is also possible to obtain $D_i(0)$ by obtaining a frequency (a frequency not less than the threshold value) T of the multiple echo, in which the intensity of the RF signal changes significantly, and multiplying the half of the frequency T by the speed of sound C.

In addition, in regard to the initial position $D_i(0)$ of the boundary surface 22 of the elastic coupler 20, it is possible to obtain a two-dimensional distribution including the distribution in the direction perpendicular to the scanning direction.

[S7: Measurement of Coupler Deformation (Distortion)]

The processing in S7 is processing by the coupler distortion calculating unit 33. First, the coupler distortion calculating unit 33 can detect that the elastic coupler 20 is in the pressurized state based on the fact that the above-mentioned multiple echo due to the elastic coupler 20 disappears.

Method 1 for Coupler Deformation (Distortion) Measurement

The coupler distortion calculating unit 33 detects the depth position of the boundary surface 22 of the elastic coupler 20 based on the RF signal at an arbitrary timing t when the elastic coupler 20 is in the pressurized state and obtains a boundary surface position distribution Di (t) in the scanning direction in the pressurized state of the elastic coupler 20. That is, the boundary surface position distribution Di (t) in the scanning direction perpendicular to the ultrasonic beam is obtained based on the speed of sound C and half of a time ti (t) from the point in time when the operator places the probe 1 on the object 100 via the elastic coupler 20, applies the pressurizing force, and transmits the ultrasonic waves in the pressurized state to the point in time when the intensity of an RF signal Qi (t) changes significantly.

Subsequently, a boundary surface position change distribution ΔDi(t) is obtained by the following formula (1) and obtains a total distortion amount distribution Si(t) of the boundary surface 22 of the elastic coupler 20 in the scanning direction by the following formula (2).

$$\Delta Di(t) = Di(0) - Di(t) \quad (1)$$

$$Si(t) = \Delta Di(t)/Di(0) \quad (2)$$

Method 2 for Coupler Deformation (Distortion) Measurement

Instead of above Method 1, the coupler distortion calculating unit 33 can measure the distortion of the elastic coupler 20 and obtain an absolute pressure Pi (t) based on this. That is, the coupler distortion calculating unit 33 can obtain a total distortion amount Sij(t) by obtaining the displacement of the measurement point within the elastic coupler at the respective measurement points in time based on an RF signal frame data Qij(0) of the coupler echo region in the initial state, which is output from the RF signal frame data selection unit 10, and an RF signal frame data Qij(t) which is output from the RF signal frame data selection unit 10 at an arbitrary timing t in the pressurized state. Here, as described above, i represents the coordinate in the scanning direction of the elastic coupler 20, and j represents the coordinate in the thickness direction (depth direction) of the elastic coupler 20.

That is, the coupler distortion calculating unit 33 receives the RF signal Qij(t) of the coupler echo region, which changes in real time in the pressurized state, and generates the displacement frame data by obtaining the displacement at the respective measurement points i and j by a known displacement calculation method based on Qij(0) in the initial state and Qij(t) at the arbitrary timing t. Then, the distortion frame data constituted by the total distortion amount Sij(t) at the measurement points i and j is obtained by spatially differentiating the displacement frame data.

Then, an average value Si*(t) of the total distortion amount Sij(t) is obtained for the entire range of the depth j of the coupler echo region for each coordinate i in the same scanning direction based on the total distortion amount Sij(t) of the distortion frame data and evaluates the average value Si*(t) as the total distortion amount Sij(t) at the coordinate position i in the ultrasonic wave scanning direction. Then, the pressure converter 34 obtains the absolute pressure Pi(t) with the use of the evaluated total distortion amount Sij(t).

According to this method, it is possible to simultaneously perform the distortion calculation of the body tissue by the elasticity modulus calculating unit 12 in FIG. 1 and the processing for obtaining the absolute pressure Pi(t).

In the case of this method, since it is possible to strengthen the intensity of the RF signal by dispersing and mixing the ultrasonic scattering bodies in the elastic coupler 20, the accuracy in calculating the thickness or the distortion is enhanced.

Method 3 for Coupler Deformation (Distortion) Measurement

According to Method 3 for the coupler pressurization evaluation, a pair of RF signal frame data, which was obtained at different timings, is obtained from the RF signal frame data selection unit 10 in a continuous manner at the respective measurement points in time from the initial state to the pressurized state. Then, distortion changes ΔSij (t−k), . . . , ΔSij(t) at the measurement points i and j are obtained for all the regions up to the boundary surface 22 of the elastic coupler 20 every time the pair of RF signal frame data is obtained. Thereafter, distortion change ΔSi, j(t) of a timing (t−1) and the timing (t), for example, which are temporally adjacent to each other, is obtained. Furthermore, distortion changes ΔSi, j(t−k), . . . , ΔSi, j(t) are sequentially summed up for the temporally continuous pair of RF signal frame data, and a distortion change summed-up value ΣΔSij(t) at the present point in time is obtained. Then, ΣΔSij(t) at the measurement points i and j is averaged in the direction of the coordinate j of the coupler echo region to obtain a distortion change summed-up value ΣΔSi*(t) for the measurement point i is obtained.

[S8: Conversion Processing of Absolute Pressure]

The pressure converter 34 reads the elasticity property (Young's modulus E, for example) corresponding to the ID of the elastic coupler 20, which has been identified by the coupler ID identification unit 31, from the coupler database 36 and converts the distortion Si(t) obtained by Method 1 with the coupler distortion calculating unit 33 into an absolute pressure Pi (t) applied to the body tissue of the object 100 by the following formula (3).

$$Pi(t) = Si(t) \times E \quad (3)$$

The current absolute pressure Pi (t) obtained by the conversion is output to the elastic modulus calculating unit 12 in FIG. 1. With this operation, the elastic modulus calculating unit 12 obtains an elastic modulus (for example, Young's modulus) Eij(t) at the respective measurement points and j by the following formula (4) based on distortion εij(t) obtained for the respective measurement points i, j of the body tissue by the known calculation processing as described above, and outputs the elastic modulus to the elasticity data processing unit 13.

$$Eij(t) = Pi(t)/\epsilon ij(t) \quad (4)$$

The total distortion amount Sij(t) obtained based on the average value Si*(t) in Method 2 by the coupler distortion calculating unit 33 or the distortion change summed-up value ΣΔSi*(t) obtained by Method 3 is converted into the absolute pressure Pi (t) by the following formulae (5) and (6). In addition, the pressure converter 34 may be integrally formed with the coupler distortion calculating unit 33.

$$Pi(t) = Si^*(t) \times E \quad (5)$$

$$Pi(t) = \Sigma \Delta Si^*(t) \times E \quad (6)$$

[S9: Display Processing of Pressure Distribution]

The pressurizing-state image constructing unit 35 creates an image of the absolute pressure Pi(t) obtained by the conversion processing of the absolute pressure in S8, prompts the image display 9 to display the created image, and thereby makes it possible for the operator to immediately determine whether or not the pressurizing state is appropriate for the test item in the same screen while executing the ultrasound test.

That is, the pressurizing-state image constructing unit 35 constructs at least one image from among the numerical value display, the graph display of the temporal change, the bar chart display, and the like from the absolute pressure Pi(t), converts the image into color image data by the color scan converter 14, and display the converted image while aligning or partially overlapping it with the ultrasonic image displayed on the image display 9.

Figure 7:
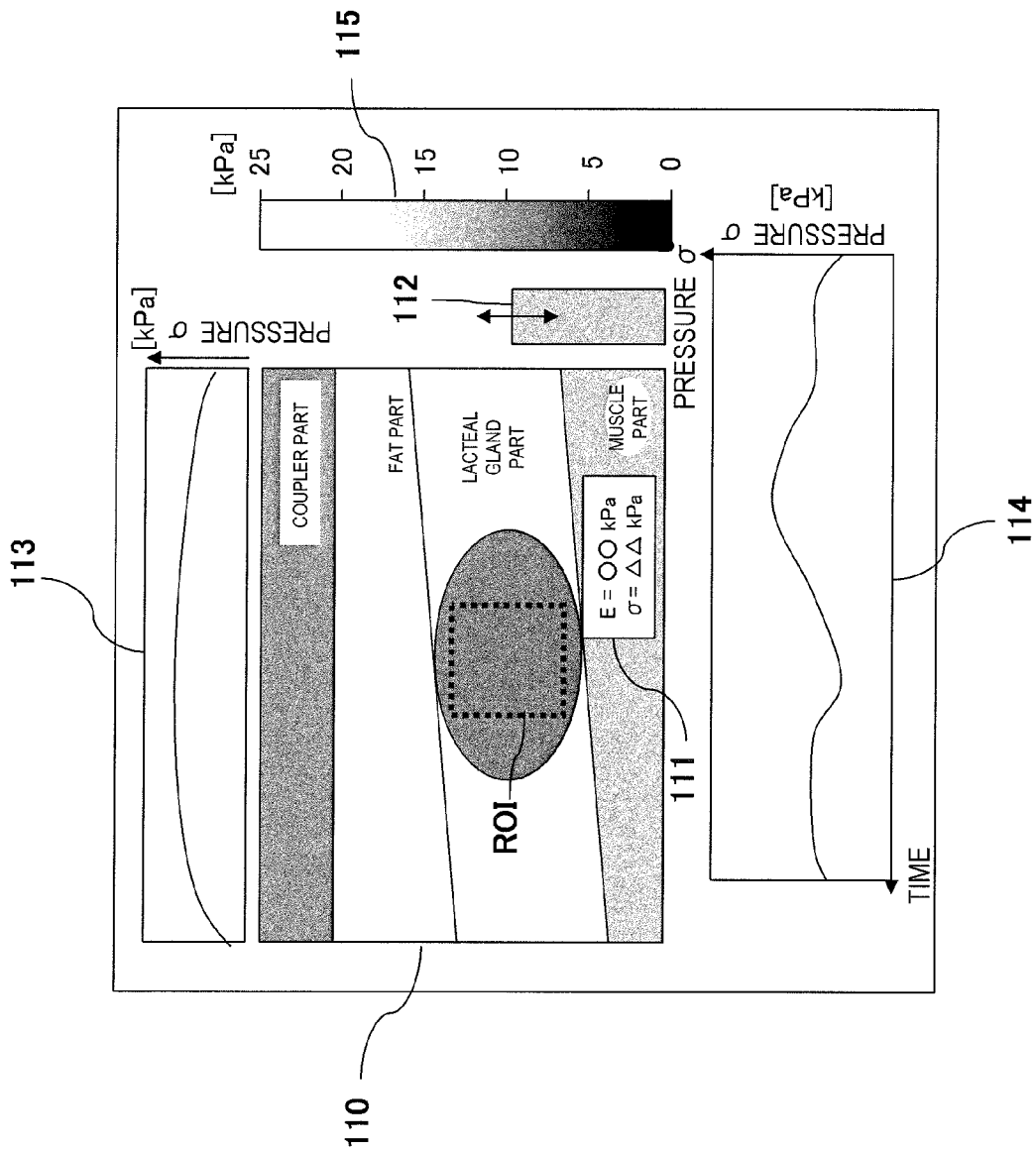
FIG. 7 is a diagram illustrating an example of a pressurizing-state image.

FIG. 7 shows an example in which the pressurizing-state image is overlapped or aligned with the elasticity image. In the drawing, an elasticity image 110 is displayed in the center of the screen, and an elastic modulus E (kPa) and an absolute pressure σ (kPa) are displayed as numerical values in a display window 111 near the rectangular site of interest (ROI). In addition, a bar chart 112 is displayed in which the absolute pressure G at present is an average value of the absolute pressure Pi. Moreover, a graph 113 of the absolute pressure Pi in the scanning direction is displayed in the upper part of the screen, and a graph 114 of the temporal change in the average value of the absolute pressure Pi is displayed in the lower part of the screen. Furthermore, a color bar 115 of the elastic modulus E is displayed at the right edge of the screen.

Accordingly, the operator can perform diagnosis while evaluating the elasticity of the body tissue of the ROI under an appropriate absolute pressure by observing the image in FIG. 7. Particularly, it is possible to immediately determine whether or not the pressurizing force is appropriate by checking the bar chart 112 of the average value or the like of the absolute pressure Pi.

Figure 8:
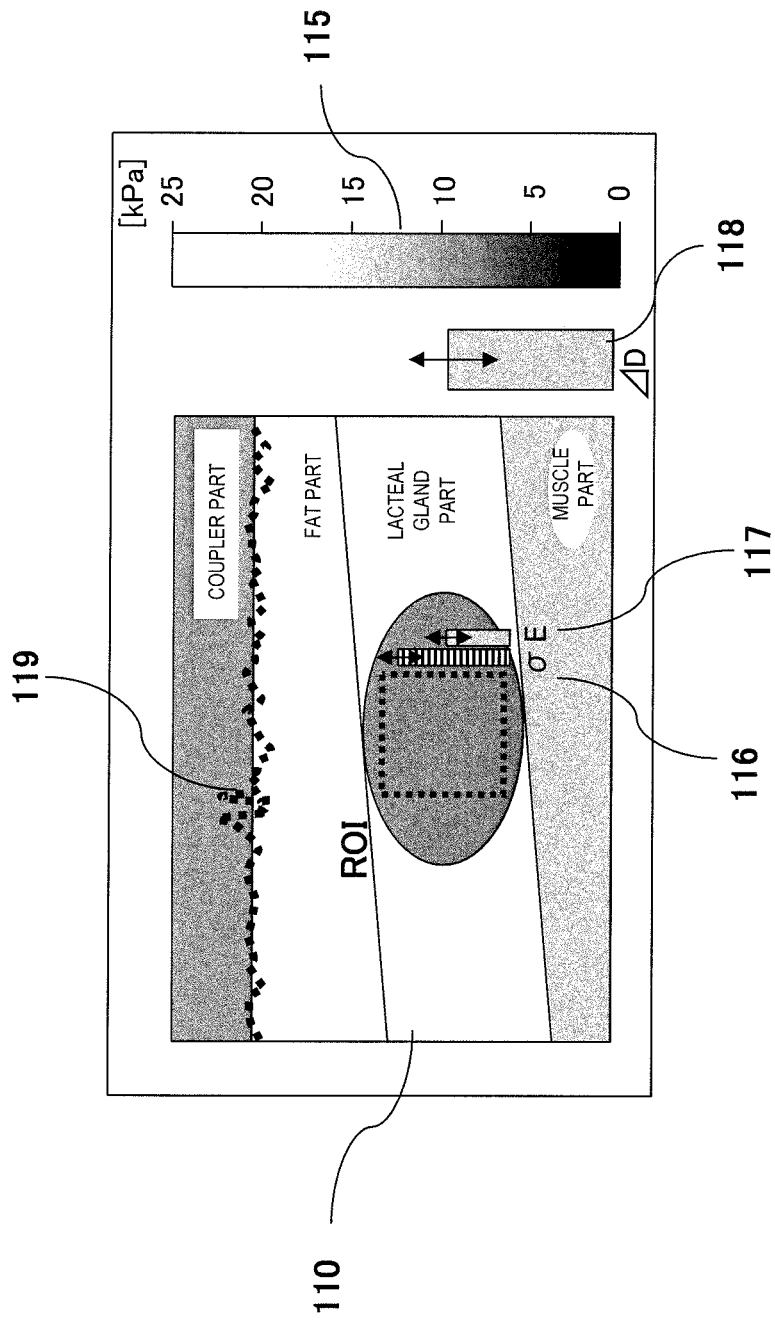
FIG. 8 is a diagram illustrating another example of the pressurizing-state image.

FIG. 8 shows another example in which the pressurizing-state image is displayed while being overlapped or aligned with the elasticity image. In the same drawing, the elasticity image 110 is displayed in the center of the screen, and the elastic modulus E (kPa) and the absolute pressure σ (kPa) are displayed in bar charts 116 and 117 near the rectangular site of interest (ROI). In addition, a bar chart 118 representing the average value of the thickness change ΔDi(t) of the elastic coupler from the initial state is displayed. Moreover, the boundary between the elastic coupler and the object is displayed by a plurality of dots 119 in the upper part of the screen.

It is possible to easily identify whether or not the pressurizing state is appropriate by changing the displaying color of the boundary representing, for example, the ROI or by turning on and off the display of the boundary when the absolute pressure, which is the calculation result by the pressure calculating unit 30, is compared with a reference pressure range, which has been set to correspond to the test method, and the absolute pressure exceeds the reference pressure range.

As described above, according to this embodiment, it is possible to accurately measure the absolute pressure applied to the body tissue of the object 100 by the probe 1 in real time in the test processing of the ordinary elasticity image measurement.

In addition, since the ID code of the elastic coupler can be read during the elasticity image measurement processing, it is possible to automatically identify the elastic coupler and accurately measure the absolute pressure in accordance with the elasticity property of the elastic coupler even if various different elastic couplers are arbitrarily replaced. Therefore, it is possible to reduce the burden of the operator and thereby to enhance usability.

Although the description was made of the example of the ultrasonic diagnostic apparatus for creating and displaying the elasticity image in this embodiment, the present invention is not limited thereto and can be applied to an ultrasonic diagnostic apparatus for performing tests such as a diagnosis by a tomographic image (B mode image) of the body tissue of the object, and a bloodstream diagnosis by the Doppler measurement or the color flow mode (CFM). Accordingly, it is possible to accurately execute the evaluation of the pressurized state suitable for various tests.

Here, a description will be made of another example of the elastic coupler.

FIG. 9(A) shows a perspective view of Example 2 of the elastic coupler 20. It is possible to use the same attachment tool as that shown in FIG. 3. As shown in FIG. 9(A), the elastic coupler in Example 2 is different from the elastic coupler 20 in Example 1 shown in FIG. 2(A) in that a thin intermediate layer 20C is formed to be interposed between the boundary surfaces of the two layers 20A and 20B with the same ultrasonic wave reflectance properties. The ultrasonic wave reflectance property of the intermediate layer 20C is made to be different from those of the other two layers 20A and 20B. In such a case, the reflection intensity of the intermediate layer 20C may be higher or lower than those of the other two layers 20A and 20B. An example of the B mode image 101 in such a case will be shown in FIG. 9(B). As shown in the same drawing, an echo image of the intermediate layer 20C appears at the boundary between the two layers 20A and 20B of the elastic coupler 20 in the upper part of the image.

In such a case, the coupler ID identification unit 31 can identify the ID code of the elastic coupler based on the distribution of the RF signal in the thickness direction in the same manner as in Example 1. In addition, a configuration can be made such that the coupler distortion calculating unit 33 obtains the positional change of the intermediate layer 20C in the thickness direction, the distortion of the intermediate layer 20C in the thickness direction, or the summed-up value of the distortion, which is obtained by summing up the distortions of the intermediate layer 20C in the thickness direction over the passage of time from the initial state of the elastic coupler with no pressure being applied and obtains the absolute pressure applied to the object in the same manner as in Example 1.

Moreover, FIG. 10(A) shows a perspective view of Example 3 of the elastic coupler 20. It is possible to use the same attachment tool as that shown in FIG. 3. The elastic coupler of Example 3 is different from the elastic coupler 20 in Example 2 shown in FIG. 9(A) in that a plurality of linear ultrasonic wave reflection bodies 20D are provided instead of the intermediate layer 20C so as to extend in a direction perpendicular to the scanning direction of the ultrasonic beam of the probe 1 and be spaced from each other.

In Example 3 as well, it is possible to identify the ID code of the elastic coupler based on the position of the ultrasonic wave reflection bodies 20D in the depth direction and detect the absolute pressure based on the positional change of the ultrasonic wave reflection bodies 20D in the same manner as in Example 2.

Moreover, although not shown in the drawing, a configuration can be made such that the layer (20A in the example shown in FIG. 2(A)) on the side of the contact surface which is in contact with the body surface of the object 100 from among the layers 20A and 20B in Example 1 is formed to be thinner and have a stronger ultrasonic wave reflectance property.

Furthermore, the ID code is given in a manner such that the ultrasonic scattering bodies are dispersed and mixed entirely in the elastic coupler 20 and the dispersion densities of the scattering bodies are made to be different. As the ultrasonic scattering bodies, it is possible to use a material such as graphite powder or polyethylene powder which has a different acoustic impedance from that of the material of the elastic coupler 20.

Furthermore, it is also possible to give an ID code in accordance with the type of the elastic coupler 20 by forming a code region, in which the scattering bodies coded in the scanning direction are dispersed, at least in one of the regions in the both ends of the elastic coupler 20 in the scanning direction, which are apart from the site of interest (ROI).

In addition, in any one of Examples 1 to 3 of the elastic coupler 20, it is possible to increase the attenuation of the ultrasonic waves by mixing the ultrasonic scattering bodies in the whole of the elastic coupler 20.

Here, the principle of detecting the absolute pressure according to the present invention is based on the fact that the thickness of the elastic coupler 20 changes in correlation with an applied pressurizing force (pressure) and that the correlation depends on the elasticity property of the elastic coupler 20. Thus, it is necessary to measure in advance the elasticity property for each type of the elastic coupler 20 and set the elasticity property corresponding to the ID code of the elastic coupler 20 in the coupler database in order to obtain the absolute pressure.

Here, in regard to the elasticity property set in the coupler database, the elastic modulus E may be set to correspond to the ID code when the deformation (distortion) of the boundary surface or the intermediate layer in the thickness direction has a linear shape with respect to the absolute pressure or when the elastic modulus (for example, Young's modulus) of the elastic coupler 20 is constant (linear).

A relation curve between the deformation (distortion) in the thickness direction and the absolute pressure or a relation curve between the deformation (distortion) in the thickness direction and the elastic modulus E is set when the positional change of the boundary surface or the intermediate layer in the thickness direction has a non-linear shape with respect to the absolute pressure or when the elastic modulus E has a non-linear shape with respect to the absolute pressure. Alternatively, it is possible to set a relation curve between the summed-up value of the deformations or the distortions in the thickness direction and the elastic modulus, or an elastic modulus correction coefficient with respect to the deformation (distortion) in the thickness direction.

As described above, according to this embodiment, it is possible to accurately measure the absolute pressure applied to the body tissue of the object 100 by the probe 1 in real time in the test processing of the ordinary elasticity image measurement.

In addition, since the ID code of the elastic coupler can be read during the elasticity image measurement processing, it is possible to automatically identify the elastic coupler and accurately measure the absolute pressure in accordance with the elasticity property of the elastic coupler even if various different elastic couplers are arbitrarily replaced. Therefore, it is possible to reduce the burden of the operator and thereby to enhance usability.

Although the description was made of the example of the ultrasonic diagnostic apparatus for creating and displaying the elasticity image in this embodiment, the present invention is not limited thereto and can be applied to an ultrasonic diagnostic apparatus for performing tests such as a diagnosis by a tomographic image (B mode image) of the body tissue of the object, and a bloodstream diagnosis by the Doppler measurement or the color flow mode (CFM). Accordingly, it is possible to accurately execute the evaluation of the pressurizing state suitable for various tests.

The invention claimed is:

1. An ultrasonic diagnostic apparatus including an ultrasonic probe configured to transmit and receive ultrasonic waves while in contact with an object, a transmitting unit configured to drive the ultrasonic probe, a receiving unit configured to receive and process an RF signal which is a reflected echo signal received by the ultrasonic probe, and an image creating unit configured to create an ultrasonic image based on the RF signal output from the receiving unit, comprising:

an elastic coupler attached to an ultrasonic wave transmitter/receiver surface of the ultrasonic probe and including at least two plate-shaped layers disposed on each other, each of the at least two plate-shaped layers having a different ultrasonic wave reflectance property from each other; and a pressure calculating unit configured to obtain the pressure applied to the object based on the reflected echo signal and the deformation of the elastic coupler, wherein the pressure calculating unit is configured to:
perform a detect operation to detect, via the reflected echo signal, a detected position of a boundary surface between the at least two plate-shaped layers of the elastic coupler, with the pressure applied to the object, determine a positional change of the boundary surface caused by the pressure applied to the object, using both the detected position of the boundary surface from the detect operation and an initial position of the boundary surface which has been obtained in advance, where the initial position concerns a position of the boundary surface with the pressure not applied to the object, and calculate an absolute pressure applied to the object, based on the positional change from the determine operation and based on an elasticity property of the elastic coupler.

2. The ultrasonic diagnostic apparatus according to claim 1, wherein the boundary surface between the at least two plate-shaped layers with different ultrasonic wave reflectance properties is disposed between an attachment surface which is attached to the ultrasonic wave transmitter/receiver surface and a contact surface which is for contact with the body surface of the object, and wherein the pressure calculating unit detects a displacement of the position of the boundary surface in the thickness direction of the elastic coupler based on frame data of a pair of RF signals which was obtained at different timings and output from the receiving unit, obtains a distortion of the boundary surface in the thickness direction based on the displacement, and obtains the absolute pressure applied to the object based on the distortion in the thickness direction and the pre-set elasticity property of the elastic coupler.

3. The ultrasonic diagnostic apparatus according to claim 2, wherein the pressure calculating unit sums up the distortions of the boundary surface over time from the initial state of the elastic coupler with no pressure being applied and obtains the absolute pressure applied to the object based on a summed-up value of the distortion and the pre-set elasticity property of the elastic coupler.

4. The ultrasonic diagnostic apparatus according to claim 1, wherein the elastic coupler is formed to have an intermediate layer interposed between the boundary surface and an ultrasonic wave reflectance property of the intermediate layer is formed to be different from those of the other layers, and wherein the pressure calculating unit detects a position of the intermediate layer in a thickness direction, obtains the positional change of the intermediate layer based on the detected position of the intermediate layer and the initial position of the intermediate layer, which was obtained in advance, and obtains the absolute pressure applied to the object based on the positional change and the pre-set elasticity property of the elastic coupler.

5. The ultrasonic diagnostic apparatus according to claim 2, wherein the elastic coupler is formed to have an intermediate layer interposed between the boundary surface and an ultrasonic wave reflectance property of the intermediate layer is formed to be different from those of the other layers, and wherein the pressure calculating unit detects the displacement of the position of the intermediate layer of the elastic coupler in the thickness direction based on the pair of RF signal frame data which was obtained at different timings and output from the receiving unit, obtains the distortion of the intermediate layer in the thickness direction based on the displacement, and obtains the absolute pressure applied to the object based on the distortion in the thickness direction and the pre-set elasticity property of the elastic coupler.

6. The ultrasonic diagnostic apparatus according to claim 3, wherein the elastic coupler is formed to have an intermediate layer interposed between the boundary surface and an ultrasonic wave reflectance property of the intermediate layer is formed to be different from those of the other layers, and wherein the pressure calculating unit sums up the distortions of the intermediate layer in the thickness direction over the passage of time from the initial state of the elastic coupler with no pressure being applied and obtains the absolute pressure applied to the object based on the distortion summed-up value and the pre-set elasticity property of the elastic coupler.

7. The ultrasonic diagnostic apparatus according to claim 4, wherein the intermediate layer includes a plurality of linear ultrasonic wave reflection bodies which extend in a direction perpendicular to a scanning direction of the ultrasonic beam of the ultrasonic probe and are spaced from each other.

8. The ultrasonic diagnostic apparatus according to claim 1, wherein a layer on the side of a contact surface which is in contact with the body surface of the object is formed to be thinner than a layer on the side of a contact surface which is in contact with the ultrasonic wave transmitter/receiver surface and to have a stronger ultrasonic wave reflectance property.

9. The ultrasonic diagnostic apparatus according to claim 1, wherein the elastic coupler is formed by mixing ultrasonic scattering bodies in an elastic material to increase an ultrasonic wave attenuation property.

10. The ultrasonic diagnostic apparatus according to claim 1, wherein an identification code, with which the type of the elastic coupler is identified by the RF signal, is formed for the elastic coupler by making the position of the boundary surface in the thickness direction be different in accordance with the type of the elastic coupler, and wherein the pressure calculating unit identifies the type of the elastic coupler by detecting an identification code based on the RF signal or an RF signal frame data and obtains the absolute pressure based on the elasticity property which is set to correspond to the type of the elastic coupler.

11. The ultrasonic diagnostic apparatus according to claim 10, wherein the identification code is formed by making the position of the boundary surface in the thickness direction be different, and wherein the pressure calculating unit identifies the type of the elastic coupler based on a depth distribution pattern of the RF signal within a coupler echo region based on the RF signal or RF signal frame data.

12. The ultrasonic diagnostic apparatus according to claim 10, wherein the identification code is formed by encoding and dispersing ultrasonic scattering bodies in at least one of the scanning direction and the thickness direction in regions of both ends of the elastic coupler in the scanning direction, and wherein the pressure calculating unit identifies the type of the elastic coupler based on an RF signal pattern in the regions of both ends of the elastic coupler based on the RF signal or the RF signal frame data.

13. The ultrasonic diagnostic apparatus according to claim 1, wherein the elasticity property of the elastic coupler is at least one of an elastic modulus, a relation curve between the deformation in the thickness direction and the elastic modulus, a relation curve between the distortion in the thickness direction and the elastic modulus, a relation curve between the summed-up value of the deformations or the distortions in the thickness direction and the elastic modulus, and an elastic modulus correction coefficient with respect to the deformation or the distortion in the thickness direction.

14. An ultrasonic diagnostic apparatus including an ultrasonic probe configured to transmit and receive ultrasonic waves while in contact with an object, a transmitting unit configured to drive the ultrasonic probe, a receiving unit configured to receive and process an RF signal which is a reflected echo signal received by the ultrasonic probe, and an image creating unit configured to create an ultrasonic image based on the RF signal output from the receiving unit, comprising:

an elastic coupler attached to an ultrasonic wave transmitter/receiver surface of the ultrasonic probe and including at least two plate-shaped layers disposed on each other, each of the at least two plate-shaped layers having a different ultrasonic wave reflectance property from each other and each of the at least two plate-shaped layers having an initial thickness in an initial non-pressurized state with a boundary surface being defined as an interface between the at least two plate-shaped layers; and a pressure calculating unit configured to obtain the pressure applied to the object based on the reflected echo signal and the deformation of the elastic coupler, wherein the pressure calculating unit is configured to:
perform a detect operation to detect, via the reflected echo signal when pressure is applied to the object, a detected position of the boundary surface between the at least two plate-shaped layers of the elastic coupler due to a thickness change of the at least two plate-shaped layers, perform a determining operation to determine a positional change of the boundary surface due to the thickness change caused by the pressure applied to the object, using both the detected position of the boundary surface from the detect operation and an initial position of the boundary surface which has been obtained in advance, where the initial position concerns a position of the boundary surface in the initial non-pressurized state with said each of the at least two plate-shaped layers having the initial thickness, and calculate an absolute pressure applied to the object, based on the positional change from the determining operation and based on an elasticity property of the elastic coupler.

15. An ultrasonic diagnostic apparatus including an ultrasonic probe configured to transmit and receive ultrasonic waves while in contact with an object, a transmitting unit configured to drive the ultrasonic probe, a receiving unit configured to receive and process an RF signal which is a reflected echo signal received by the ultrasonic probe, and an image creating unit configured to create an ultrasonic image based on the RF signal output from the receiving unit, comprising:

an elastic coupler attached to an ultrasonic wave transmitter/receiver surface of the ultrasonic probe and including at least two plate-shaped sheets of material disposed on each other, each of the at least two plate-shaped sheets of material having a different ultrasonic wave reflectance property from each other and each of the at least two plate-shaped sheets of material having an initial thickness in an initial non-pressurized state with a boundary surface being defined as an interface between the at least two plate-shaped sheets of material; and a pressure calculating unit configured to obtain the pressure applied to the object based on the reflected echo signal and the deformation of the elastic coupler, wherein the pressure calculating unit is configured to:

perform a detect operation to detect, via the reflected echo signal when pressure is applied to the object, a detected position of the boundary surface between the at least two plate-shaped sheets of material of the elastic coupler due to a thickness change of the at least two plate-shaped sheets of material, perform a determining operation to determine a positional change of the boundary surface due to the thickness change caused by the pressure applied to the object, using both the detected position of the boundary surface from the detect operation and an initial position of the boundary surface which has been obtained in advance, where the initial position concerns a position of the boundary surface in the initial non-pressurized state with said each of the at least two plate-shaped sheets of material having the initial thickness, and calculate an absolute pressure applied to the object, based on the positional change from the determining operation and based on an elasticity property of the elastic coupler.

* * * * *